US00PP31144P3

(12) United States Plant Patent
Kordes

(10) Patent No.: US PP31,144 P3
(45) Date of Patent: Dec. 3, 2019

(54) MINIATURE ROSE PLANT NAMED 'KORPOT082'

(50) Latin Name: *Rosa hybrida*
Varietal Denomination: KORpot082

(71) Applicant: W. KORDES' SÖHNE Rosenschulen GmbH & Co. KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,568

(22) Filed: Nov. 29, 2017

(65) Prior Publication Data

US 2019/0166741 P1 May 30, 2019

(30) Foreign Application Priority Data

Oct. 18, 2017 (QZ) ..... PBR 2017/2616

(51) Int. Cl.
*A01H 5/02* (2018.01)
*A01H 6/74* (2018.01)

(52) U.S. Cl.
USPC ..... Plt./118
CPC ..... *A01H 6/749* (2018.05)

(58) Field of Classification Search
USPC ..... Plt./118
CPC ..... A01H 6/749; A01H 5/02
See application file for complete search history.

(56) References Cited

U.S. PATENT DOCUMENTS

PP19,638 P2 1/2009 Kordes

*Primary Examiner* — Keith O. Robinson
(74) *Attorney, Agent, or Firm* — Buchanan Ingersoll & Rooney PC

(57) ABSTRACT

A new and distinct variety of Miniature Rose Plant, herein referred to by its cultivar name, 'KORpot082', is provided which forms in abundance on a substantially continuous basis attractive, light yellow colored blossoms. The vegetation is vigorous and the growth habit is compact. Attractive ornamental foliage is formed with good disease resistance. The new variety is particularly well suited for providing distinctive ornamentation in the landscape.

1 Drawing Sheet

Botanical/commercial classification: Latin name—*Rosa hybrida*. Common name—Miniature Rose Plant.
Varietal denomination: 'KORpot082'.

CROSS-REFERENCE TO RELATED APPLICATIONS

This application claims priority to Plant Breeder's Rights Application Number 2017/2616, which was filed in European Union through Community Plant Variety Office on Oct. 18, 2017, the contents of which are hereby expressly incorporated by reference in their entirety for all purposes.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling from a previous cross of an unnamed seedling and 'KORpedia' (U.S. Plant Pat. No. 19,638)). The male parent (i.e., pollen parent) of the new variety was an unnamed seedling.

The parentage can be summarized as follows:

(unnamed seedling x 'KORpedia') x unnamed seedling

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, light yellow colored blossoms,
(b) exhibits a compact growth habit,
(c) forms vigorous vegetation, and
(d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the (unnamed seedling x 'KORpedia') variety (i.e., seed parent) exhibits a larger leaf size and a less upright growth habit compared to the new variety, as the seed parent displays a moderately spreading growth habit, whereas the new variety displays a compact growth habit and has an improved shelf compared to the seed parent. Additionally, the unnamed seedling male parent variety (i.e., pollen parent) exhibits a lower petal count compared to the new variety and displays light pink colored flowers, whereas the new variety displays light yellow colored flowers. Further, the new variety has an improved shelf life compared to the pollen parent. Moreover, the new variety can be readily distinguished from non-parental related similar varieties. For example, the 'KORpot001' variety displays more petals and a less upright growth habit compared to the new variety and the 'KORpot001' variety exhibits cream apricot colored flowers, whereas the new variety exhibits light yellow colored flowers.

The new variety has been found to undergo asexual propagation in Klein Offenseth-Sparrieshoop, Germany by a number of routes such as vegetative cuttings. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot082'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 10.5 cm container.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during September, while growing in a one-gallon container on its own roots at Cochranville, Pa.

Class: Miniature Rose Plant.

Plant:

*Habit*.—Compact, very bushy and upright.

*Height*.—Approximately 43.0.0 cm on average in a one gallon container.

*Width*.—Approximately 30.0 cm on average in a one gallon container.

*Growth*.—Moderate.

Branches:

*Stem color*.—Young and old wood: commonly near Green Group 141C.

*Stem diameter*.—Approximately 3.0 mm on average.

*Main stem length*.—Approximately 43.0 cm on average.

*Secondary stem length*.—Approximately 15.0 cm on average.

*Surface texture*.—Old wood is glabrous; young wood is glabrous.

*Thorns*.—Young thorns: length is approximately 6.0 mm on average, width is approximately 5.0 mm at point of attachment on average, amount is moderate, and color is commonly near Greyed-Yellow Group 160C. Old thorns: length is approximately 5.0 mm on average, width is approximately 2.0 mm at point of attachment on average, amount is moderate, and color is commonly near Greyed-Orange Group 165A. Shape: erect.

Foliage:

*General appearance*.—Ornamental.

*Young foliage*.—Upper surface color: commonly near Yellow-Green Group 146B with near Greyed-Purple Group 183B at margins. Under surface color: commonly near Green Group 137C and Greyed-Purple Group 183D.

*Old foliage*.—Upper surface color: commonly near Green Group 137A. Under surface color: commonly near Green Group 138B.

*Petiole*.—Upper surface: texture is glabrous; color is commonly near Yellow-Green Group N144A. Under surface: texture is mostly glabrous with some small prickles, color is commonly near Yellow-Green Group 144A. Diameter: approximately 1.0 mm on average. Length of terminal leaflet: approximately 3.0 cm on average.

*Petiolules*.—Color is commonly near Green Group 137A, length is approximately 1.0 mm on average, and diameter is approximately 1.0 mm on average.

*Rachis*.—Color: upper surface is commonly near Yellow-Green Group 144A, under surface is commonly near Yellow-Green Group 144A. Size: length is approximately 4.0 cm on average and diameter is approximately 1.0 mm on average.

*Stipules*.—Length: approximately 5.0 mm on average. Width: approximately 2.0 mm on average. Margin: entire to erose. Shape: apiculate, base is flat. Color: upper surface is commonly near Yellow-Green Group 144A; under surface is commonly near Yellow-Green Group 144A.

*Leaf margin*.—Serrate.

*Glossiness of upper side of leaf*.—Medium.

*Leaf arrangement*.—Odd pinnate.

Leaflets:

*Number*.—3, 5, and 7.

*Shape*.—Ovate, apex is acute, base is rounded.

*Venation*.—Pattern is reticulate; color is indistinguishable.

*Texture*.—Upper surface is smooth; under surface is smooth.

*Size*.—Terminal leaflet: length is approximately 3.5 cm on average and width is approximately 2.5 cm on average. Lower leaflets: length is approximately 2.2 cm on average and width is approximately 1.6 cm on average. 5-Leaflet leaf: length is approximately 10.0 cm on average and width is approximately 6.5 cm on average.

Inflorescence:

*Flower*.—Form: double, cuplike to flat. Height: approximately 3.0 cm on average. Duration: commonly on the plant 7 to 10 days.

*Number of flowers*.—Commonly about 4 blooms on average on a plant at once.

*Number of blooms per stem or in a cluster*.—Typically 1 bloom per stem.

*Peduncle*.—Color: commonly Yellow-Green Group 144A. Diameter: approximately 3.0 mm on average. Length: approximately 3.5 cm on average. Surface texture: sparely covered in short, flexible thorns that measure less than 2.0 mm in length. Strength: medium.

*Sepals*.—Number: commonly 5. Arrangement: arranged evenly around the top of the receptacle and reflexed away from the base of the corolla. Upper surface color and texture: covered in short pubescence and color is commonly near Yellow-Green Group 144A. Under surface color and texture: puberulent and color is commonly near Yellow-Green Group 144B. Size: length is approximately 1.6 cm on average and width is approximately 6.0 mm on average. Shape: lanceolate; apex is acute to aristate, base is truncate or flat where it joins to the receptacle. Margin: entire with occasional extensions on two or three sepals measuring approximately 2.0 mm in length and approximately 1.0 mm in width.

*Bud*.—Shape: ovoid. Size: length is approximately 2.0 cm on average; width is approximately 1.5 cm on average. Color (when opening): commonly near White Group 155A.

*Fragrance*.—Very light sweet fragrance.

*Petal*.—Number: approximately 44 on average. Drop: good. Length: inner petals are approximately 1.6 cm on average; outer petals are approximately 2.5 cm on average. Width: inner petals are approximately 1.0 cm on average; outer petals are approximately 2.0 cm on average. Shape: overall shape is broadly obovate; apex is round; and base is cuneate. Margin: entire. Texture: upper and lower surfaces are glabrous. Arrangement: formal. Color upon opening: upper surface is commonly near Yellow Group 11A and under surface is commonly near Yellow Group 11B. Color when fully open: upper surface is commonly near Yellow Group 4D and near Yellow Group 13B at the point of attachment; under surface is commonly near Yellow Group 4D and commonly near Yellow Group 11A at the point of attachment. Color after opening: upper and under surfaces are commonly near White Group 155A.

*Petaloids*.—Number: between 3 and 8 on average. Shape: variable, oblong and mostly curving inward; apex is round; and base is cuneate. Size: length is approximately 1.5 cm on average and width is approximately 8.0 mm on average. Margin: variable, entire to erose. Texture: smooth. Color of upper and under surfaces: commonly near Yellow Group 5D with some highlights of near Yellow Group 13B around the margin and point of attachment.

*Basal spot*.—Absent.

*Stamen*.—Number: approximately 30 on average. Anthers: number is about 30 and color is commonly near Greyed-Yellow Group 162B; shape is oval, length is approximately 2.0 mm on average; and width is approximately 1.0 mm on average. Filaments: length is approximately 4.0 mm on average and color is commonly near Yellow-Orange Group 16A.

*Pistils*.—Arrangement: separate and free. Number: approximately 28. Length: approximately 7.0 mm on average. Style: color is commonly near Yellow-Green Group 145B; length is approximately 1.0 cm on average. Stigma: position in relation to anthers is superior; shape is fan shaped, color is commonly near Orange Group 24D; diameter is commonly less than 1.0 mm on average.

*Receptacle*.—Achenes stand on the bottom and wall; diameter is approximately 1.0 cm on average, depth is approximately 3.0 mm on average, shape is urn shaped, color is commonly near Yellow-Green Group 144A, and surface texture is smooth.

*Ovary*.—Length is approximately 2.0 mm; width is approximately 1.0 mm; and color is commonly near White Group 155B.

*Pollen*.—None observed.

*Hips/seed*.—None observed.

Development:

*Vegetation*.—Medium green, vigorous, and strong.

*Blooming*.—Abundant and substantially continuous.

*Winter hardiness or USDA hardiness zone*.—Unknown.

*Resistance to disease*.—Good resistance to Botrytis (*Botrytis cinereal*) disease under normal greenhouse growing conditions in Cochranville, Pa.

Plants of the 'KORpot082' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, light yellow colored blossoms, (b) exhibits a compact growth habit, (c) forms vigorous vegetation, and (d) forms attractive ornamental foliage with good disease resistance; substantially as herein shown and described.

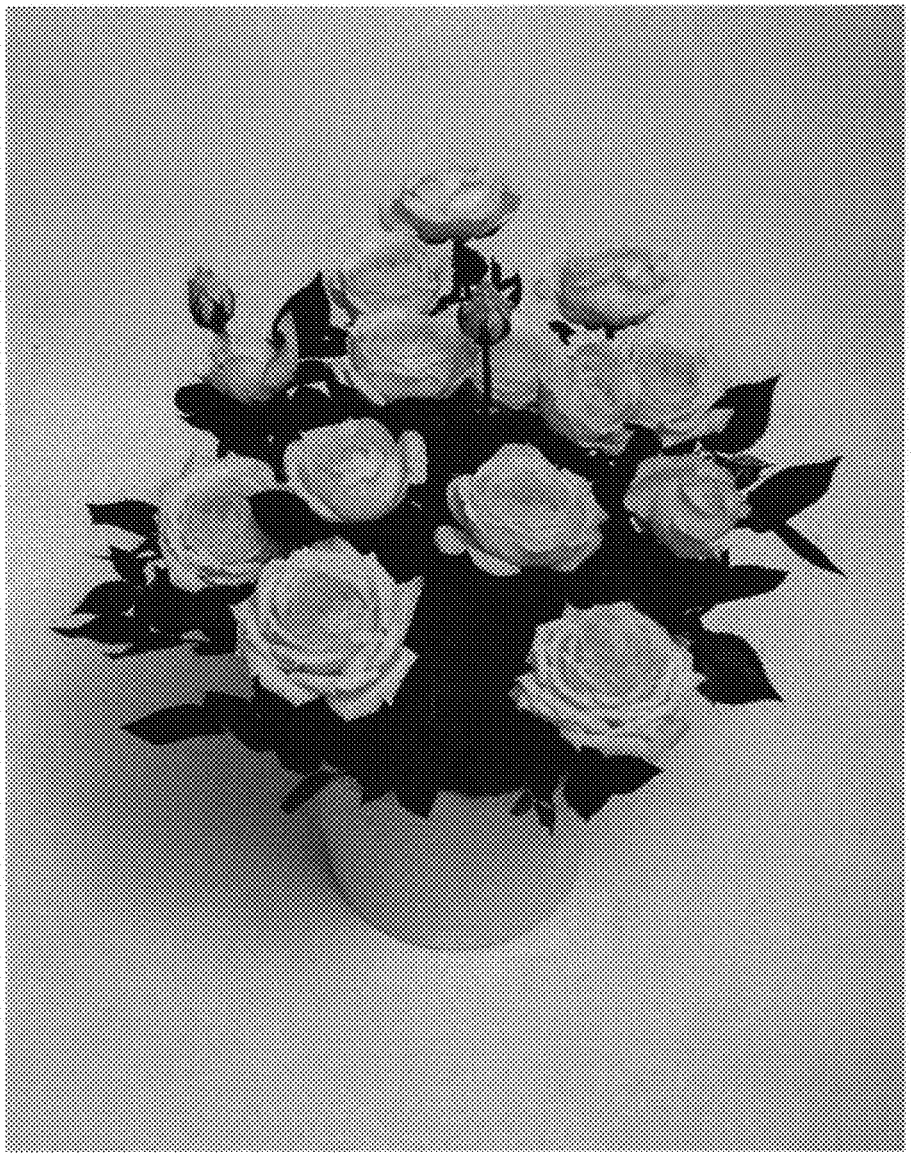

* * * * *